(12) United States Patent
Millar

(10) Patent No.: US 6,235,123 B1
(45) Date of Patent: *May 22, 2001

(54) CHEMICAL CLEANING SYSTEM FOR ELECTRODES USED IN A LIQUID ENVIRONMENT

(75) Inventor: Ord Millar, Pierrefonds (CA)

(73) Assignee: Honeywell-Measorek Corporation, Morristown, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/072,519

(22) Filed: May 4, 1998

(51) Int. Cl.$^7$ ................... B08B 3/00; B08B 5/00
(52) U.S. Cl. ................... 134/26; 134/34; 134/36; 134/37; 134/183
(58) Field of Search ................... 134/183, 26, 34, 134/36, 37, 201, 42

(56) References Cited

U.S. PATENT DOCUMENTS

| | | | |
|---|---|---|---|
| 3,625,850 | 12/1971 | Arrington | 204/402 |
| 4,377,880 * | 3/1983 | Jackson et al. | 15/302 |
| 4,687,986 * | 8/1987 | Eriksson | 324/71.1 |
| 5,373,229 * | 12/1994 | Penniman | 324/71.1 |
| 5,485,099 * | 1/1996 | Collins et al. | 324/439 |
| 5,495,751 * | 3/1996 | Petzold et al. | 73/53.03 |

FOREIGN PATENT DOCUMENTS

| | | |
|---|---|---|
| 0 372 121 | 6/1990 | (EP) . |
| 1 558 208 | 2/1969 | (FR) . |
| 92/06368 * | 4/1992 | (WO) . |
| WO 97 10384 | 3/1997 | (WO) . |

* cited by examiner

Primary Examiner—Alexander Markoff
(74) Attorney, Agent, or Firm—Anthony E. Ebert; Anthony Miologos

(57) ABSTRACT

A apparatus and method for in-situ treatment of electrodes in liquid environments in which a solution supply orifice is located near an electrode to be cleaned, and when cleaning is desired, a treatment solution from the solution supply orifice is directed against the electrode or electrodes. A cleaning baffle may be placed over the electrodes to better direct the treatment solution. The electrodes may be cleaned of the treatment solution by directing a flow of gas or a second treatment solution against the electrodes, subsequent use of the first treatment solution.

12 Claims, 2 Drawing Sheets

CHEMICAL CLEANING SYSTEM FOR ELECTRODES USED IN A LIQUID ENVIRONMENT

BACKGROUND OF THE INVENTION

1. Field of the Invention

The present invention relates generally to automatic chemical cleaning systems, and more specifically to chemical cleaning of electrodes or probes for use in liquor composition measurements in paper pulp processing.

2. Description of the Prior Art

Trees are turned into paper via a series of chemical and mechanical transformations. In the early part of this process, chips of wood are broken down or digested into wood fiber which will subsequently be passed on for mechanical processing, such as drying and pressing. During digestion, the wood chips are loaded into a tank called a digester. A caustic solution—referred to as white liquor—is added to the wood chips. The white liquor breaks down the wood chips into individual wood fibers under heat and pressure. Sodium hydroxide and sodium sulfide, for example, are one commonly used component of white liquor use to break down the wood chips.

Recovery or reclamation of the white liquor for re-use is performed as a secondary process at the paper mill. Reclamation of the caustic solution subsequent to breakdown of the wood chips is typically performed in a two step process called recausticizing in which the used caustic solution is transformed into a black, followed by a green liquor, and finally returned to its white liquor state. The caustic solution may thereafter be reused to separate wood fibers.

For optimum breakdown of the wood fibers in the digester, and for optimum reclamation of the caustic solution in the recausticizing part of the process, accurate control of the composition of the liquor in each step is important. One method of effective composition control is done using a series of electrodes embedded in a housing mounted inside the digester or recausticizing tank. The electrodes measure the chemical composition of the solution in each tank directly, and provide measurement signals to a control system, which then makes any necessary corrections to the liquor composition.

Unfortunately, the electrodes placed in the environment of the digester or recausticizing tank will be prone to buildup of waste material—called scale—during the digesting and recausticizing process steps. Keeping ahead of accumulation of scale on electrodes has long been a difficult challenge in paper mills. As scale builds up on a conventional electrode, the electrode signal drifts, resulting in inaccurate electrode signals and thus inaccurate inputs into process controllers. Historically, this has caused electrodes to be a high-maintenance item for paper mills, and resulted in low confidence in the accuracy of electrode measurements.

In the past, to address these problems the electrodes were typically cleaned or replaced every one to two weeks. During the periods of cleaning or replacement, the liquor composition must be manually controlled, or paper mill processing must be suspended.

As a relatively new alternate solution, ultrasonic cleaning of the electrodes in-situ allows cleaning of the electrode without requiring down-time of the paper mill or manual control or liquor composition. While the ultrasonic system is reliable, it unfortunately cannot keep up with the build-up of scale on the electrodes, and thus the electrodes must be periodically manually cleaned, although at less frequent intervals, than where no in-situ cleaning is performed. Furthermore, the ultrasonic energy applied to the electrodes eventually causes damage to the electrodes, making replacement necessary.

SUMMARY OF THE INVENTION

The present invention solves these and other needs by providing a method and apparatus for in-situ chemical treatment of the electrodes in liquid environments. The applicant's inventions allows the electrodes to operate on a continuous basis, as long as treatment solution is available whenever treatment of the electrodes is required.

In a preferred embodiment of the applicant's invention, a liquid cleaning solvent is provided to a location near the electrodes, and, using a movable electrode cover or cleaning baffle, cleaning solvent is directed against the electrodes until the electrodes are clean of built-up material. The electrode cover may then be moved out of the way so that the electrodes can operate normally until the next cleaning is required. A further step may be employed in which the cleaning solvent is removed from the electrodes subsequent cleaning, by directing a gas, or a liquid other than the solvent, against the electrodes, dissipating the cleaning solvent into the large tank area.

In another embodiment, the cleaning baffle is eliminated altogether and replaced by solvent directing member.

In a further embodiment, the applicant's invention is used for other purposes that to clean the electrodes, such as altering electrode temperature, or for electrode surface treatment.

DETAILED DESCRIPTION

Figure 1:
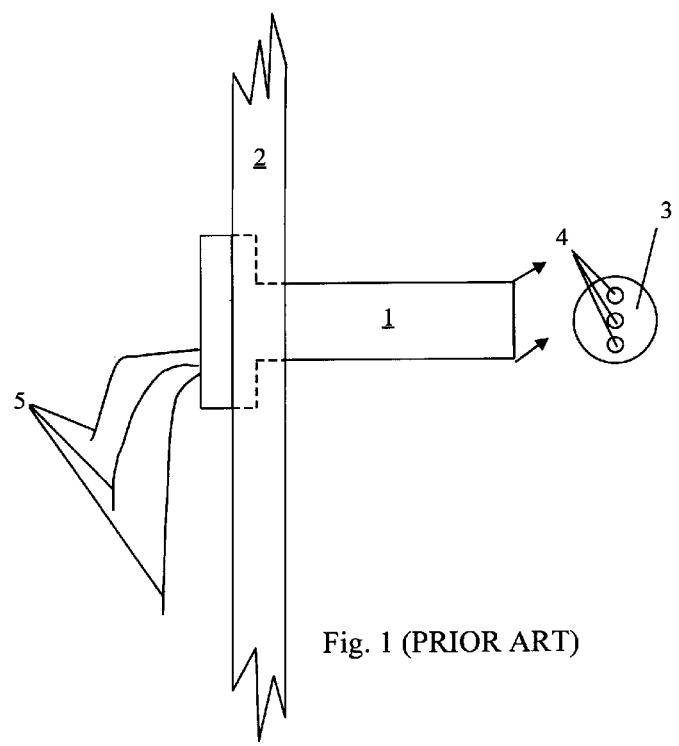
FIG. 1 shows a typical electrode arrangement of the kind commonly found in the prior art.

FIG. 1 shows a typical arrangement of the type of electrode which will benefit from the cleaning system and method of the present invention. An electrode housing 1 is sealably mounted, at a first end, in a digester or recausticizing tank 2. The location for such a housing in the tank is as is known in the art. The other end of electrode housing 1, identified as 3 in FIG. 1, and shown as a cross-sectional view, contains electrodes or probes 4, which are used to make the composition, concentration, or another type of measurement. The electrodes are embedded in the surface of housing 1 such that they are flush with surface 3 of electrode housing 1. Wires 5 electrically connected to electrodes 4 run back through electrode housing 1, and out of tank 2 to electronics which use the electrode signals, for example, to control digesting or/and recausticizing.

Alternate designs are also possible for the electrode mounting which will not change its applicability to the applicant's invention. For example, the electrodes which may also be thought of, or referred to, as probes, may be individually mounted in the tank, either with individual housings, or independently of any housing. The electrodes may also be of various shapes, nor need they be mounted flush in the surface of the housing. Furthermore while three electrodes have been shown, a larger or smaller number of electrodes may be used depending on the reader's desired measurement. For example, while the applicant has intended his design to be used where the composition of the liquor in a digester or recausticizing tank is measured with a three electrode system, the much simpler concentration measurement of the liquor may be taken with two electrodes. This alternate type of configuration would not effect the applicability of the applicant's invention.

Figure 2:
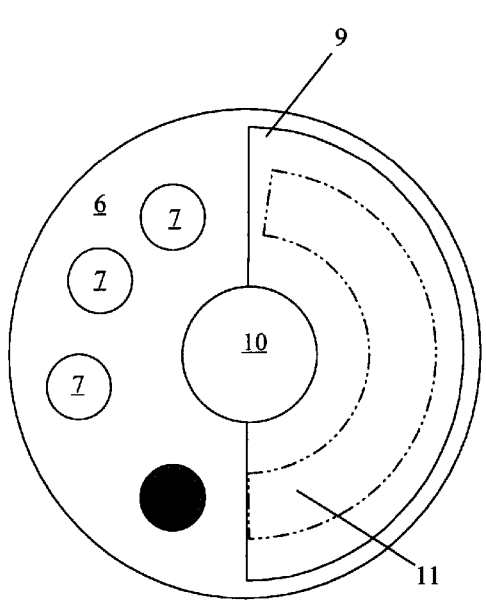
FIG. 2 shows an end view of an electrode housing, including the applicant's invention, during normal operation of the electrode.
Figure 3:
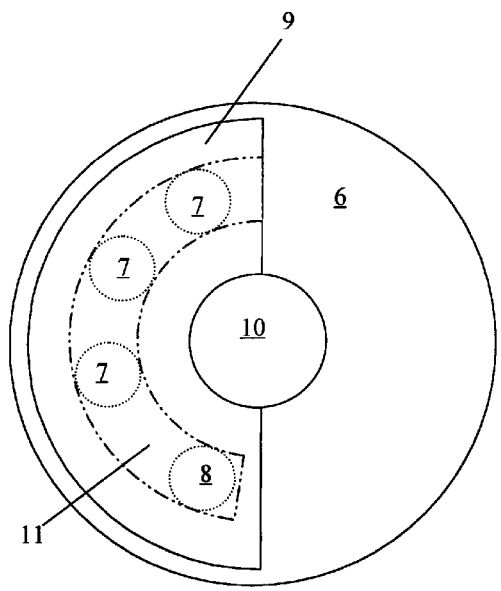
FIG. 3 shows an end view of an electrode housing, including the applicant's invention, when the cleaning system is in operation.
Figure 4:
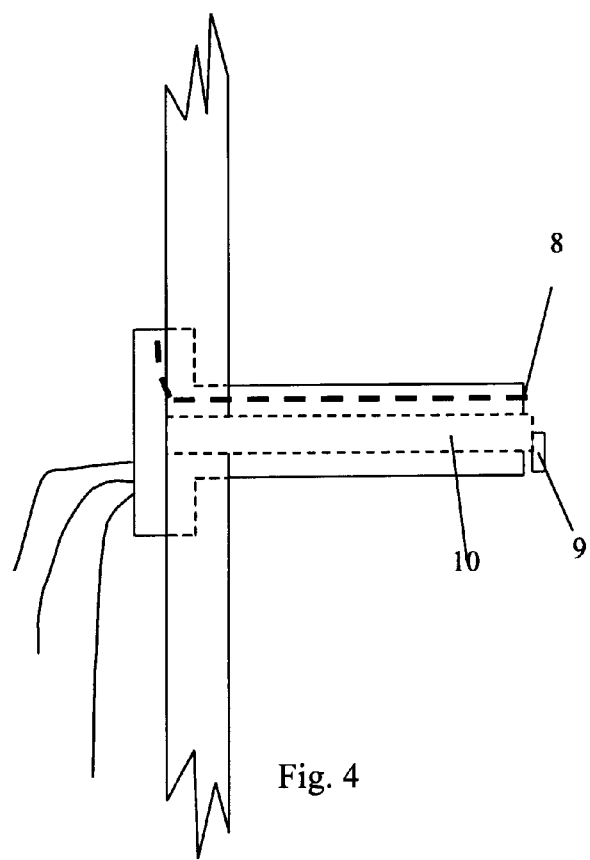
FIG. 4 shows a side view of the applicant's electrode housing design, including the applicant's cleaning system.

In any event, FIG. 2 shows an end view of a housing 6 including one embodiment of the applicant's invention. Three electrodes 7 are embedded in the surface of housing 6 on one side. A solvent, or solution, supply orifice 8 is also cut into this surface, adjacent the electrodes. The solvent supply orifice is connected to a supply of liquid cleaning solvent or other treatment solution external to the tank containing the electrode. The treatment solution should be capable of cleaning or otherwise treating the electrodes, as desired by the designer. Semi-circular member 9, which may also be identified as a cleaning baffle, lies slightly above the surface of housing 6, and is attached to a shaft 10, as shown in FIG. 4. The end of shaft 10 may also be seen as the central smaller circle in FIGS. 2 and 3.

In the illustrated embodiment, when the electrodes are in use, cleaning baffle 9 lies in a first position, adjacent the electrodes, as shown in FIG. 2, where it will not interfere with contact between liquor from the tank and the electrodes. When cleaning is desired, cleaning baffle 9 is rotated to a second position, using shaft 10, so that the cleaning baffle covers electrodes 7 and the solvent supply orifice 8, as shown in FIG. 3. When the cleaning baffle is in the position shown in FIG. 3, cleaning solvent, supplied under pressure, exits solvent supply orifice 8, hits the face of cleaning baffle 9, sprays along the underside of the baffle, and past electrodes 7. The spraying action will remove any material on the electrode surfaces which has built up during normal operation of the electrodes.

In a particularly preferred embodiment of the invention, a groove or solvent channel 11 is cut into the surface of cleaning baffle 9, facing electrodes 7, and solvent supply orifice 8. Groove 11 concentrates the flow of cleaning solvent over the electrodes when they are being cleaned, by more effectively guiding cleaning solvent from solvent supply orifice 8 to the location of electrodes 7.

While not necessary for the applicant's invention, a purging step may be added subsequent electrode cleaning to free the electrodes of cleaning solvent clinging to the electrode surface. This step may prevent erroneous electrode measurements caused by the cleaning solvent. The purging step is accomplished by spraying a gas or liquid over the electrodes via either the solvent supply orifice, or via a secondary orifice. The gas or liquid will cause any cleaning solvents or remnants of another treatment solution first applied and which remains on the electrodes, to be washed, or blown, away and diluted in the tank containing the electrodes. For reference, when a second solution is applied to the electrodes following an initial treatment or cleaning, the first applied solution may be called and will be referred to a first treatment solution, and the second applied solution may be called, and will be referred to as a second treatment solution.

During normal operation of the electrodes (i.e. when they are not being cleaned) the cleaning baffle is moved to a position adjacent the electrodes, as shown in FIG. 2. Movement of the cleaning baffle, as indicated earlier, is performed via shaft 10, which is connected to an actuator. The actuator may, for example, be a small electric motor, compressed air mechanism providing rotational motion, or some other form of rotary actuator. Alternately shaft 10 may be connected to a handle, crank, or other manual lever which will allow manual movement of the shaft from the cleaning position to the position for normal operation of the electrodes.

In another possible embodiment of the applicant's invention, cleaning baffle 9 may be of indeterminate shape, and hinged to move from the cleaning position to the position for normal operation of the electrodes. In this embodiment, a lever or other transport mechanism would be used to move the cover between the two positions. In a further embodiment, the cleaning baffle may be mounted on one or more tracks which allow it to slide from its cleaning position to the position for normal operation of the electrodes. The reader will be aware of other methods of mounting to cover so that it may be moved between its tow position. Such method are not excluded from the applicant's intended application of the ideas herein described.

If the electrodes are not flush with the surface of the electrode, more complicated baffle systems may be required. For example, if the electrodes extrude from the surface of the electrode housing some distance, the baffle may comprise a tubular shape which fits loosely over the surface of the electrode when the electrode is being cleaned. The baffle could be moved out to cover the electrodes during cleaning, or the electrodes could be retracted into the electrode housing where the cleaning would take place.

Figure 5:
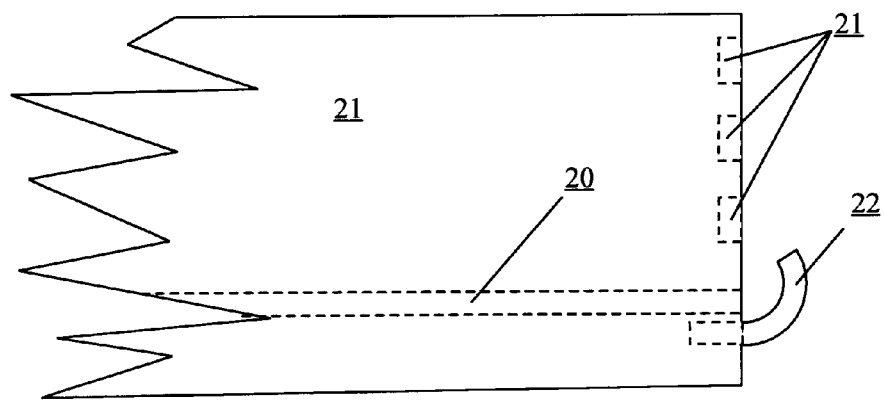
FIG. 5 shows a further embodiment including the applicant's invention.

In fact, the applicant contemplates that the baffle may be eliminated altogether, provided that the solvent is somehow directed against the electrodes during cleaning, and that this apparatus, when not in use, does not interfere with the normal operation of the electrodes. One possible system which eliminate the baffles is shown in FIG. 5. Solvent supply orifice 20 in housing 21 includes a solvent director 22, which directs solvent toward electrodes 23. The reader will of course be aware of further concepts for directing solvent from the solvent supply orifice toward the electrodes, and each of these methods is contemplated as applicable to the applicant's invention.

While location of the solvent supply orifice has been provided in the surface of the electrode housing, as shown in FIGS. 2 and 3, this location is only one possible option. Any location for the solvent supply orifice which allows direction of cleaning solvent against the electrodes is satisfactory. For example, the solvent may be supplied to the cleaning baffle itself, if passages are added in the cleaning baffle to allow direction of the solvent through the cleaning baffle, and to the electrodes. As a further alternative, the solvent supply orifice may be mounted external to the electrode housing and cleaning baffle altogether, in a separate structure.

Liquid solvent for cleaning the electrodes may be created and stored as a liquid beforehand, or it may be created as needed for cleaning, from a powder. For example, if the solvent is to be made from a powder just prior to cleaning, water may be supplied to a powder solvent reservoir, and water mixed with the powder exits the solvent reservoir to a passage leading to the solvent supply orifice.

The applicant also notes at this point that while the electrodes in the described embodiments are being cleaned by the liquid supplied from the solvent supply orifice, other types of treatment may actually be performed with the applicant's system. For example, the applicant's system may be used to maintain the electrodes in a desired temperature range, or to coat the electrodes with a protective substance. Thus, reference to cleaning in the embodiments described should be thought of more generally in terms of treatment of the electrodes, and not only applicable to cleaning of the electrodes.

Regardless of the embodiment, the solvent supply mechanism should include the necessary valves, check valves and bypasses, so that tank liquor does not leak backward into the solvent supply, and so that the electrode housing may be removed for maintenance when necessary. Particularly, the supply connection between the solvent supply and the solvent supply orifice should include a check valve to prevent liquor from escaping backwards into the electrode housing. A valve, open during electrode cleaning, and otherwise closed should also be included in the line supplying solvent, or possible earlier, in a water line, if the solvent is not pre-mixed.

Preferably, in cleaning applications, the solvent is supplied under pressure to increase its effectiveness against the built-up materials on the electrodes. If the tank containing the electrodes is pressurized, sufficient solvent pressure will be required to overcome the tank pressure.

The materials used for the various components in this applicant's system must be able to withstand the corrosive environment of the liquor. Furthermore, any components such as the surface of the electrode housing containing the electrodes, and the cleaning baffle, must be able to withstand the corrosiveness of the solvent as well and the liquor. One common material which meets these requirements is a nickel-molybdenum-chromium-tungsten alloy commonly known as Hastelloy-C 276, which is particularly resistant to Sulfamic acid, a preferred solvent for use in the digester and recausticizing tanks. Of course, other materials may be desirable, based on the composition of the liquor, and the solvents to which the various parts will be exposed.

Since the invention disclosed herein may be embodied in other specific forms without departing from the spirit or general characteristics thereof, some of which forms have been indicated, the embodiments described herein are to be considered in all respects illustrative and not restrictive. For example, while the applicant's invention has been described in terms of composition measurement or concentration measurement in digester and recausticizing tanks, it is also suitable for ORP, Ion Selective, Voltameteric Measuring systems, thermocouple temperature measurement, liquid level monitoring or other types of systems utilizing electrodes or probes in liquid solutions. Further, applications outside the paper-making industry are contemplated, in any place where a liquid environment is used. The scope of the invention is to be indicated by the appended claims, rather than by the foregoing description, and all changes which come within the meaning and range of equivalency of the claims are intended to be embraced therein.

What is claimed is:

1. A method for in-situ cleaning of electrodes the electrodes being mounted within an electrode housing, and having a surface in communication with a liquid to be measured comprising:

providing a cleaning solvent to a solvent supply orifice via said electrode housing, said solvent supply orifice adjacent an electrode to be cleaned;

causing a cleaning baffle having a solvent channel extending along a surface of the cleaning baffle directly facing the electrode and supply orifice to move be rotated from a first position adjacent the electrode to a second position covering the surface of the electrode wherein when the cleaning baffle is said first position, analysis of the liquid to be measured occurs, and when the cleaning baffle is in the second position, cleaning of said electrode occurs; and directing the cleaning solvent from the solvent supply orifice, across the surface of the of the electrode using the solvent channel, when the cleaning baffle is in the second position.

2. The method of claim 1 wherein:

the cleaning baffle is connected to an actuator via a transport mechanism; and movement of the cleaning baffle from the first position to the second portion is accomplished via the transport mechanism by activating the actuator.

3. The method of claim 2 wherein:

the actuator is a rotary actuator; and the transport mechanism comprises a shaft connecting the rotary actuator to the cleaning baffle.

4. The method of claim 1, further comprising the step of forcing a gas in said cleaning baffle solvent channel subsequent electrode cleaning and while the cleaning baffle is still in the second position, to dissipate cleaning solvent from the region around the electrode.

5. The method of claim 1 further comprising the step of forcing a liquid other than solvent in said cleaning baffle solvent channel subsequent electrode cleaning and while the cleaning baffle is still in the second position, to dissipate cleaning solvent from the area around the electrode.

6. The method of claim 1 wherein one cleaning baffle is used to cover more than one electrode, when said cleaning baffle is in said second position.

7. An apparatus for in-situ cleaning of electrodes used in caustic liquid environments to analyze a liquid to be measured and mounted in an electrode housing comprising:

a solvent supply orifice mounted in said electrode housing, and adjacent the electrode;

an cleaning baffle rotatably mounted along a shaft that is centrally located on said electrode housing said cleaning baffle rotatable between a first and second position, the first position being adjacent the electrode wherein analysis of the liquid to be measured occurs, and when the cleaning baffle is in said second position cleaning of said electrode occurs, said cleaning baffle further including a solvent channel extending along a surface of the cleaning baffle directly facing the electrode and supply orifice; and means for rotating said cleaning baffle from said first position to said second position wherein in said second position said solvent channel covers said electrode and said solvent supply orifice and solvent from the solvent supply orifice flows within said solvent channel across the surface of the electrode cleaning said electrode.

8. The apparatus of claim 7 wherein one cleaning baffle is used to cover more than one electrode, when said cleaning baffle is rotated into said second position.

9. The apparatus of claim 7 wherein the means for rotating said cleaning baffle comprises:

an actuator connected to said shaft; and whereby movement of the cleaning baffle from the first position to the second position is accomplished via said shaft by activating the actuator.

10. The apparatus of claim 9 wherein said actuator is a rotary actuator that rotates said shaft thereby rotating said cleaning baffle from said first position to said second position.

11. The apparatus of claim 7 wherein the means for rotating the cleaning baffle comprises a manual lever.

12. The apparatus of claim 7 wherein the cleaning baffle is composed of a nickel-molybdenum-chromium-tungsten alloy.

* * * * *